(12) United States Patent
Jeong et al.

(10) Patent No.: US 9,835,852 B2
(45) Date of Patent: Dec. 5, 2017

(54) SCANNER FOR TWO-DIMENSIONAL OPTICAL SCANNING, MANUFACTURING METHOD THEREOF, AND MEDICAL IMAGING APPARATUS USING THE SAME

(71) Applicant: Korea Advanced Institute of Science and Technology, Daejeon (KR)

(72) Inventors: Ki-Hun Jeong, Daejeon (KR); Yeong-Hyeon Seo, Daejeon (KR); Hyeon Cheol Park, Daejeon (KR); Kyung Min Hwang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 408 days.

(21) Appl. No.: 14/567,025

(22) Filed: Dec. 11, 2014

(65) Prior Publication Data

US 2016/0051131 A1    Feb. 25, 2016

(30) Foreign Application Priority Data

Aug. 25, 2014  (KR) ................ 10-2014-0110670
Nov. 10, 2014  (KR) ................ 10-2014-0155229

(51) Int. Cl.
*A61B 6/00* (2006.01)
*G02B 26/10* (2006.01)
*A61B 1/00* (2006.01)
*G02B 3/00* (2006.01)

(52) U.S. Cl.
CPC .......... *G02B 26/103* (2013.01); *A61B 1/0011* (2013.01); *A61B 1/00096* (2013.01); *A61B 1/00172* (2013.01); *G02B 26/101* (2013.01); *G02B 3/0087* (2013.01)

(58) Field of Classification Search
CPC .................. A61B 1/00096; A61B 1/00172
USPC .......................................... 600/478
See application file for complete search history.

(56) References Cited

U.S. PATENT DOCUMENTS 7,129,472 B1 * 10/2006 Okawa ............. A61B 1/00059
                                                      250/216

FOREIGN PATENT DOCUMENTS

KR       1020120129361       11/2012

* cited by examiner

*Primary Examiner* — Amanda Patton
*Assistant Examiner* — Philip C Edwards
(74) *Attorney, Agent, or Firm* — Cantor Colburn LLP

(57) ABSTRACT

Provided are a scanner for two-dimensional optical scanning capable of implementing two-dimensional driving by one input signal without an additional structure for modulating a resonance frequency using modulation of the resonance frequency through asymmetry of the scanner itself, and a manufacturing method thereof. In addition, there is provided a manufacturing method of a scanner for two-dimensional optical scanning capable of implementing compact packaging through a micro electro mechanical systems (MEMS) process to miniaturize the scanner, such that it may be used in a micro-miniature system such as an endoscope and capable of increasing precision of the scanner and manufacturing the scanner in various shapes and at a low cost. Further, there is provided a medical imaging apparatus using a scanner for two-dimensional optical scanning capable of providing a medical image having improved quality without crosstalk between axes through separation of resonance frequencies.

16 Claims, 10 Drawing Sheets

$$\omega = \sqrt{\frac{K_{eff}}{m_{eff}}}$$

$$K = \frac{(K_{cantil} + K_{fiber1}) * K_{fiber2}}{K_{cantil} + K_{fiber1} + K_{fiber2}} \quad \text{EQUATION (1)}$$

$K_{cantil-x}$ : stiff $K_{cantil-y}$ : flexible $$K_x = K_{fiber2}$$

$$K_y = \frac{K_{cantil-y} + K_{fiber1}}{K_{cantil-y} + K_{fiber1} + K_{fiber2}} * K_{fiber2} \quad \text{EQUATION (2)}$$

SOI Wafer

SCANNER FOR TWO-DIMENSIONAL OPTICAL SCANNING, MANUFACTURING METHOD THEREOF, AND MEDICAL IMAGING APPARATUS USING THE SAME

CROSS-REFERENCE TO RELATED APPLICATIONS

This application claims priority under 35 U.S.C. §119 to Korean Patent Application No. 10-2014-0110670 filed on Aug. 25, 2014 and 10-2014-0155229 filed on Nov. 10, 2014 in the Korean Intellectual Property Office, the disclosure of which is incorporated herein by reference in its entirety.

TECHNICAL FIELD

The following disclosure relates to a scanning apparatus for combining a laser scanning based bio imaging system with a micro-miniature system such as an endoscope. More specifically, the following disclosure relates to a scanner for two-dimensional optical scanning capable of implementing two-dimensional scanning by only one-dimensional driving through an asymmetrical structure of the scanner itself and frequency modulation, a manufacturing method thereof, and a medical imaging apparatus using the same.

BACKGROUND

An optical fiber scanner, which is a device for obtaining an external image using an optical fiber, may easily approach a photographing target and be easily manipulated, such that it is used in various industrial fields. Particularly, miniaturization of a device is easy, such that utilization of the optical fiber scanner as a medical scanner and a scanner of an endoscope is high.

Figure 1:
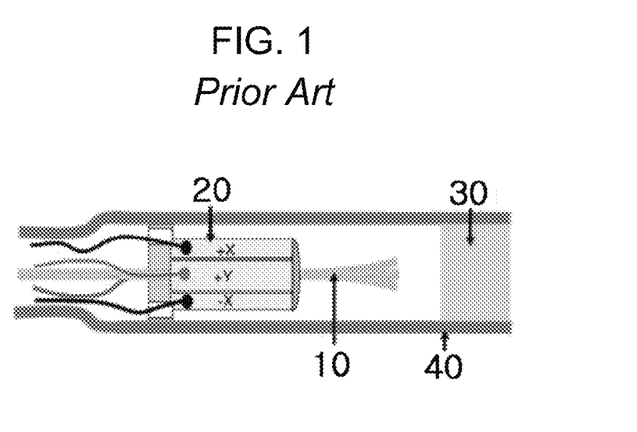
FIG. 1 is a schematic view showing an optical fiber scanner including a driver according to the related art.

FIG. 1 is a schematic view showing an optical fiber scanner according to the related art.

As shown in FIG. 1, the optical fiber scanner according to the related art is configured to include a driving means 20 disposed at one end of an optical fiber 10 and vibrating the optical fiber 10, a lens 30 disposed at the other end of the optical fiber and focusing light, and a housing 40 in which the optical fiber 10, the driving means 20, and the lens 30 are disposed. Here, as the driving means 20, a micro motor, a piezoelectric, a complementary metal oxide semiconductor-micro electro mechanical systems (CMOS-MEMS) mirror, or an MEMS mirror may be used.

In the related art, in the case in which the driving means is configured at a micro-miniature size (radius of 2 mm or less), since driving displacement of the driving means is fine, scanning displacement of the optical fiber has been limited to a predetermined range. Therefore, a method of extending the scanning displacement of the optical fiber by driving the driving means at a resonance frequency of the optical fiber has been used. Here, in the case in which the driving means is driven at the resonance frequency of the optical fiber, the scanning displacement of the optical fiber is extended by a resonance phenomenon of the optical fiber.

Here, in order for the optical fiber to have a scanning speed (resonance frequency) of 100 Hz or less, the optical fiber should have a very long length of 30 mm or more. Therefore, a method of installing a separate mass body at an end portion of the optical fiber to increase effective mass of the optical fiber has been suggested.

Figure 2:
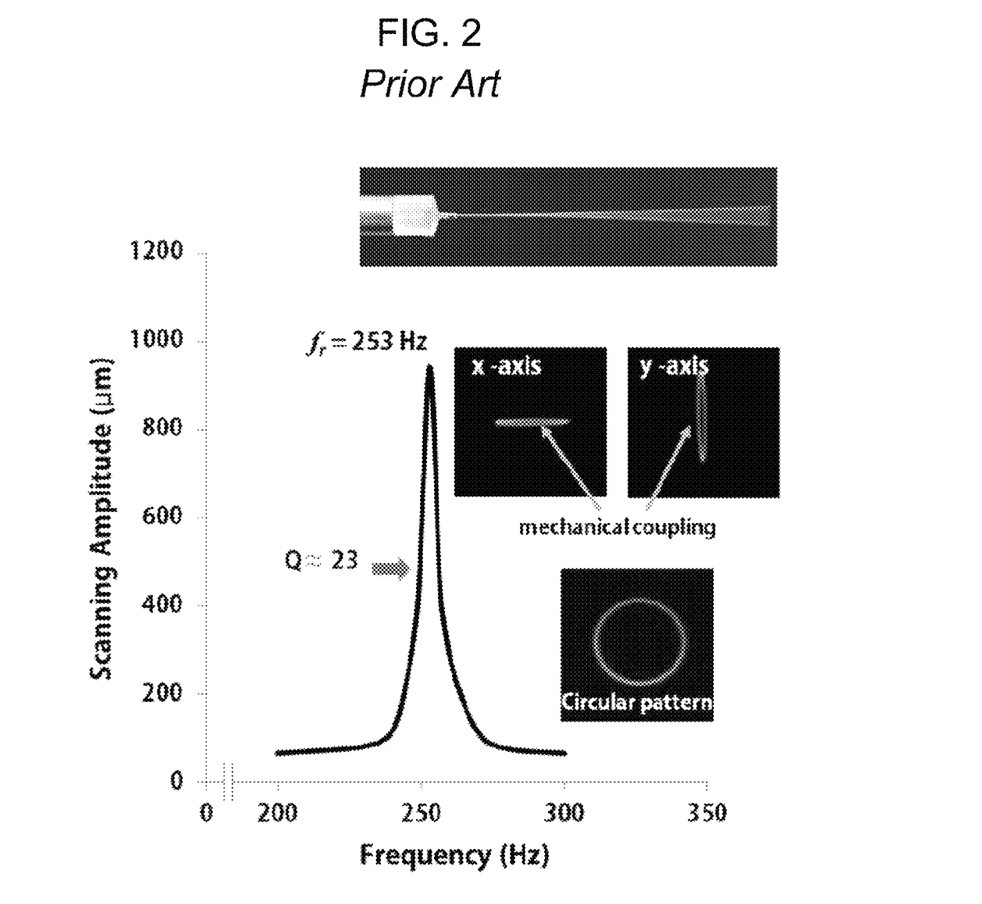
FIG. 2 is a schematic view showing a scan pattern of an optical fiber driven at a resonance frequency of the optical fiber scanner according to the related art.

However, in the related art, as shown in FIG. 2, since both of the optical fiber and the mass body are circularly formed so as to be symmetrical in X and Y directions, a resonance frequency of the optical fiber in the X direction and a resonance frequency of the optical fiber in the Y direction are the same as each other, such that only circular scanning is possible in a two-dimensional driving pattern of the optical fiber. As a result, there is a problem that only spiral scanning using amplitude modulation is possible in the optical fiber.

In addition, there is a scanner using a driver using a piezoelectric (PZT) element. However, since a very high cost is required for manufacturing a PZT tube, it is difficult to commercialize the scanner using the driver using the PZT element.

Therefore, development of an optical fiber scanner for solving the above-mentioned problems has been demanded.

RELATED ART DOCUMENT

Patent Document

KR 10-1262174 (2013 May 2)

SUMMARY

An embodiment of the present invention is directed to providing a scanner for two-dimensional optical scanning capable of implementing two-dimensional driving by one input signal without an additional structure for modulating a resonance frequency using modulation of the resonance frequency through asymmetry of the scanner itself, a manufacturing method thereof, and a medical imaging apparatus using the same.

In one general aspect, a scanner for two-dimensional optical scanning includes: a first fixing part; a second fixing part disposed so as to be spaced apart from the first fixing part; two or more driving arms having both ends connected and fixed to the first and second fixing parts, formed as one set and formed so that end portions thereof fixed to the second fixing part are electrically connected to each other, and formed so that a resonance frequency in an X axis direction and a resonance frequency in a Y axis direction are different from each other; and an optical fiber having one side fixed to the first fixing part and the other side fixed to the second fixing part, disposed so as to be spaced apart from one side of the driving arms in a width direction, and disposed at a height different from that of the driving arms in a height direction.

A spring constant of an X axis direction structure and a spring constant of a Y axis direction structure may be different from each other.

Resonance frequencies of the optical fiber in the X and Y axis directions may be separated from each other by a difference between the spring constants.

Two sets of driving arms may be spaced apart from each other and be disposed in a pair, two end portions of the driving arms fixed to the second fixing part and formed as one set may be electrically connected to each other, such that the two sets of driving arms are electrically connected to each other, respectively, and the optical fiber may be disposed between a pair of driving arms and be disposed at the height different from that of the driving arms in the height direction.

When a current is applied to one set of driving arms, movement of the second fixing part in the X and Y axis directions may occur by thermal expansion of the driving arms.

The current may include the resonance frequency in the X axis direction or the resonance frequency in the Y axis direction or include both of the resonance frequency in the X axis direction and the resonance frequency in the Y axis direction.

The first fixing part may include an insulating layer formed on a fixing block, the insulating layer having one ends of the driving arms fixed to an upper side thereof.

The fixing block and the insulating layer of the first fixing part, the driving arms, and the second fixing part may be assembled to each other to form one piece.

The first fixing part may have a fixing groove formed at a lower side thereof, and one side of the optical fiber may be inserted into and fixed to the fixing groove and the other side thereof may be fixed to a lower surface of the second fixing part.

The driving arms may have electrodes attached to one ends thereof fixed to the first fixing part.

The scanner for two-dimensional optical scanning may further include connecting parts having both ends connected and fixed to the first and second fixing parts.

The scanner for two-dimensional optical scanning may further include a probe body having an internal space formed therein so as to accommodate the first fixing part, the second fixing part, the driving arms, and the optical fiber therein and including a light input part and a light output part.

A lens unit including one or more lens may be further disposed in a light path between the optical fiber and the light output part within the probe body.

The lens unit may include a graded index (GRIN) lens.

A light path changing component may be further disposed between the lens unit and the light output part within the probe body.

The light path changing component may be formed of a reflection mirror.

The light path changing component may be formed of a prism.

In another general aspect, a medical imaging apparatus includes: a light source unit; the scanner for two-dimensional optical scanning as described above scanning-irradiating light from the light source unit to a test target; a receiving unit receiving a signal generated from the test target; and a signal processing unit processing the signal received by the receiving unit to generate an image signal.

The signal processing unit may process the received signal by any one of the laser based imaging methods.

In still another general aspect, a manufacturing method of a scanner for two-dimensional optical scanning includes: preparing a silicon-on-insulator (SOI) wafer in which a silicon dioxide layer is formed between a lower silicon layer and an upper silicon layer; etching a portion of the upper silicon layer to form shapes of driving arms and a second fixing part; etching a portion of the lower silicon layer to form a first fixing part and forming a fixing groove in the first fixing part; etching the silicon dioxide layer exposed by the etched portion of the lower silicon layer to form a shape in which both ends of the driving arms are connected to the first and second fixing parts; and inserting and fixing one side of an optical fiber into the fixing groove of the first fixing part and fixing the other side of the optical fiber to a lower surface of the second fixing part.

The first and second fixing parts may be formed so as to be spaced apart from each other, two or more driving arms may be formed as a set, be formed so that end portions thereof fixed to the second fixing part are electrically connected to each other, and be formed so that a resonance frequency in an X axis direction and a resonance frequency in a Y axis direction are different from each other, and the optical fiber may be disposed so as to be spaced apart from one side of the driving arms in a width direction and be disposed at a height different from that of the driving arms in a height direction.

Two sets of driving arms may be spaced apart from each other and be disposed in a pair, two end portions of the driving arms fixed to the second fixing part and formed as one set may be electrically connected to each other, such that the two sets of driving arms are electrically connected to each other, respectively, and the optical fiber may be disposed between a pair of driving arms and be disposed at the height different from that of the driving arm in the height direction.

The manufacturing method of a scanner for two-dimensional optical scanning may further include attaching electrodes to one ends of the driving arms fixed to the first fixing part.

[Detailed Description of Main Elements]

1000: scanner for two-dimensional optical scanning
100: first fixing part
110: fixing block  111: fixing groove

[Detailed Description of Main Elements]

120: insulating layer
200: second fixing part
300: driving arm
400: optical fiber
500: electrode
600: connecting part
700: probe body
701: support
710: light input part
720: light output part
730: lens unit
740: light path changing component (prism)
750: light path changing component (reflection mirror)
2000: medical imaging apparatus
1100: light source unit
1200: receiving unit
1300: signal processing unit
1400: controlling unit
1500: user interface
1600: test target

DETAILED DESCRIPTION OF EMBODIMENTS

Hereinafter, a technical spirit of the present invention will be described in more detail with reference to the accompanying drawings.

The accompanying drawings are only examples shown in order to describe the technical idea of the present invention in more detail. Therefore, the technical idea of the present invention is not limited to shapes of the accompanying drawings.

Figure 3:
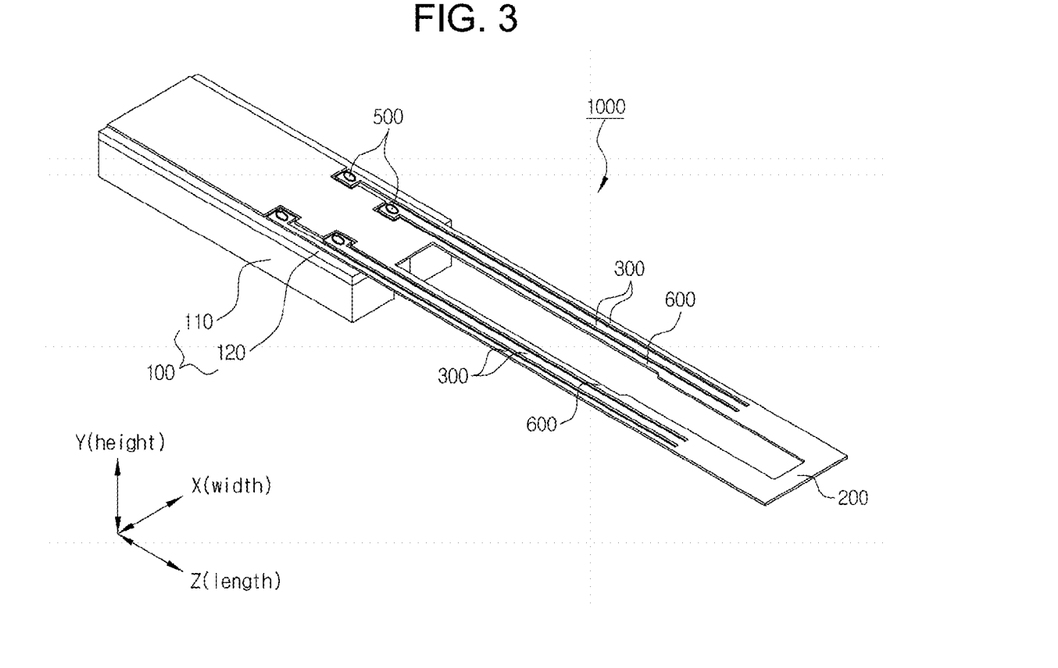
FIGS. 3 and 4 are, respectively, a top perspective view and a bottom perspective view showing a scanner for two-dimensional optical scanning according to an exemplary embodiment of the present invention in a state which an optical fiber is excluded.
Figure 4:
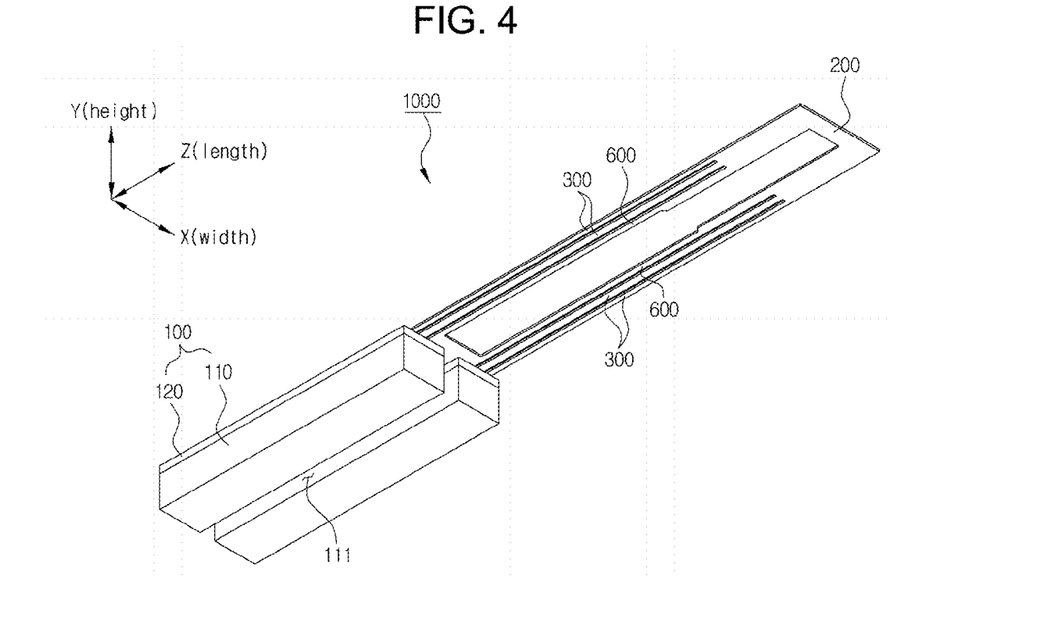
Figure 5:
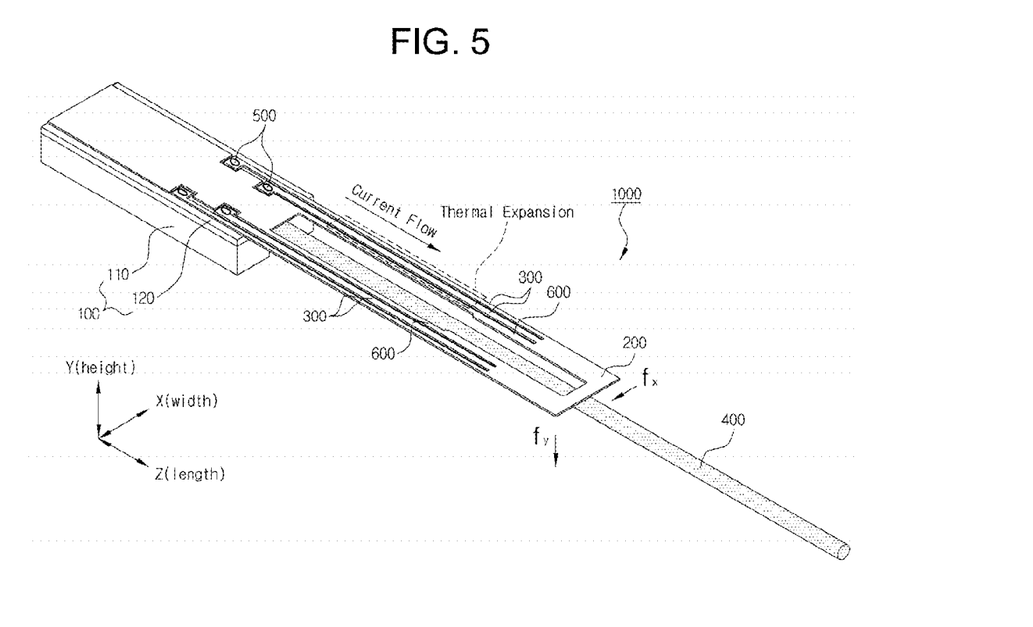
FIG. 5 is a perspective view showing the scanner for two-dimensional optical scanning according to an exemplary embodiment of the present invention including the optical fiber.

FIGS. 3 and 4 are, respectively, a top perspective view and a bottom perspective view showing a scanner for two-dimensional optical scanning according to an exemplary embodiment of the present invention in a state which an optical fiber is excluded; and FIG. 5 is a perspective view showing the scanner for two-dimensional optical scanning according to an exemplary embodiment of the present invention including the optical fiber.

As shown in FIGS. 3 to 5, the scanner 1000 for two-dimensional optical scanning according to an exemplary embodiment of the present invention may be configured to include a first fixing part 100; a second fixing part disposed so as to be spaced apart from the first fixing part 100; two or more driving arms 300 having both ends connected and fixed to the first and second fixing parts 100 and 200, formed as one set and formed so that end portions thereof fixed to the second fixing part 200 are electrically connected to each other, and formed so that a resonance frequency in an X axis direction and a resonance frequency in a Y axis direction are different from each other; and an optical fiber 400 having one side fixed to the first fixing part 100 and the other side fixed to the second fixing part 200, disposed so as to be spaced apart from one side of the driving arms 300 in a width direction, and disposed at a height different from that of the driving arms 300 in a height direction.

First, the first and second fixing parts 100 and 200 are parts to which the driving arms 300 and the optical fiber 400 are fixed, and both ends of the driving arms 300 are each connected and fixed to the first and second fixing parts 100 and 200 spaced apart from each other in a length direction (a Z axis direction). Here, the first fixing part 100 may be generally formed of an insulator and may include an insulating layer 120 formed on a fixing block 110, wherein the insulating layer 120 may have one ends of the driving arms 300 fixed to an upper side thereof.

The second fixing part 200 may have the other ends of the driving arms 300 connected and fixed thereto, and may be formed of an electrical conductor so that two or more driving arms 300 formed as one set may be electrically connected and be formed in a plate shape.

The two or more driving arms 300 are formed as one set, two driving arms 300 are disposed so as to be spaced apart from each other in the width direction, and one set of driving arms 300 are disposed on an XZ plane, which is a horizontal surface. In addition, the driving arms 300 may be formed in various forms so that the resonance frequency in the X axis direction and the resonance frequency in the Y axis direction are different from each other, and may be formed in any shape other than a shape shown.

The optical fiber 400 has one side fixed to the first fixing part 100 and the other side fixed to the second fixing part 200. Here, the optical fiber 400 fixed to the second fixing part 200 may be formed in a shape in which it is extended in the length direction, such that it may be formed in a cantilever shape at the second fixing part 200. In addition, the optical fiber 400 is disposed so as to be spaced apart from one side of the driving arms 300 in the width direction and is disposed at the height different from that of the driving arms 300 in the height direction. That is, the optical fiber 400 is disposed at one side of the driving arms 300 in the width direction and at a lower side of the driving arms 300 in the height direction, such that one side of the optical fiber 400 may be fixed to a fixing groove 111 of the first fixing part 100 and the other side thereof may be fixed to a lower surface of the second fixing part 200.

Here, the optical fiber 400 may be disposed in parallel with the driving arms 300 and be disposed in a form in which it is slightly obliquely inclined. In addition, a laser irradiator is connected to one side of the optical fiber 400 fixed to the first fixing part 100, such that the optical fiber may receive laser from the laser irradiator and output laser light.

Therefore, the driving arms 300 are extended from the first fixing part 100, the second fixing part 200 is formed in a cantilever shape at end portions of the driving arms 300, and the second fixing part 200 to which the optical fiber 400 is connected and fixed and the driving arms 300 are formed in an asymmetrical shape, a shape in which they are disposed on a horizontal surface, such that the resonance frequencies in the X and Y axis directions are differently modulated, thereby making it possible to implement two-dimensional driving by one input signal without an additional structure for modulating the resonance frequency.

Figure 6:
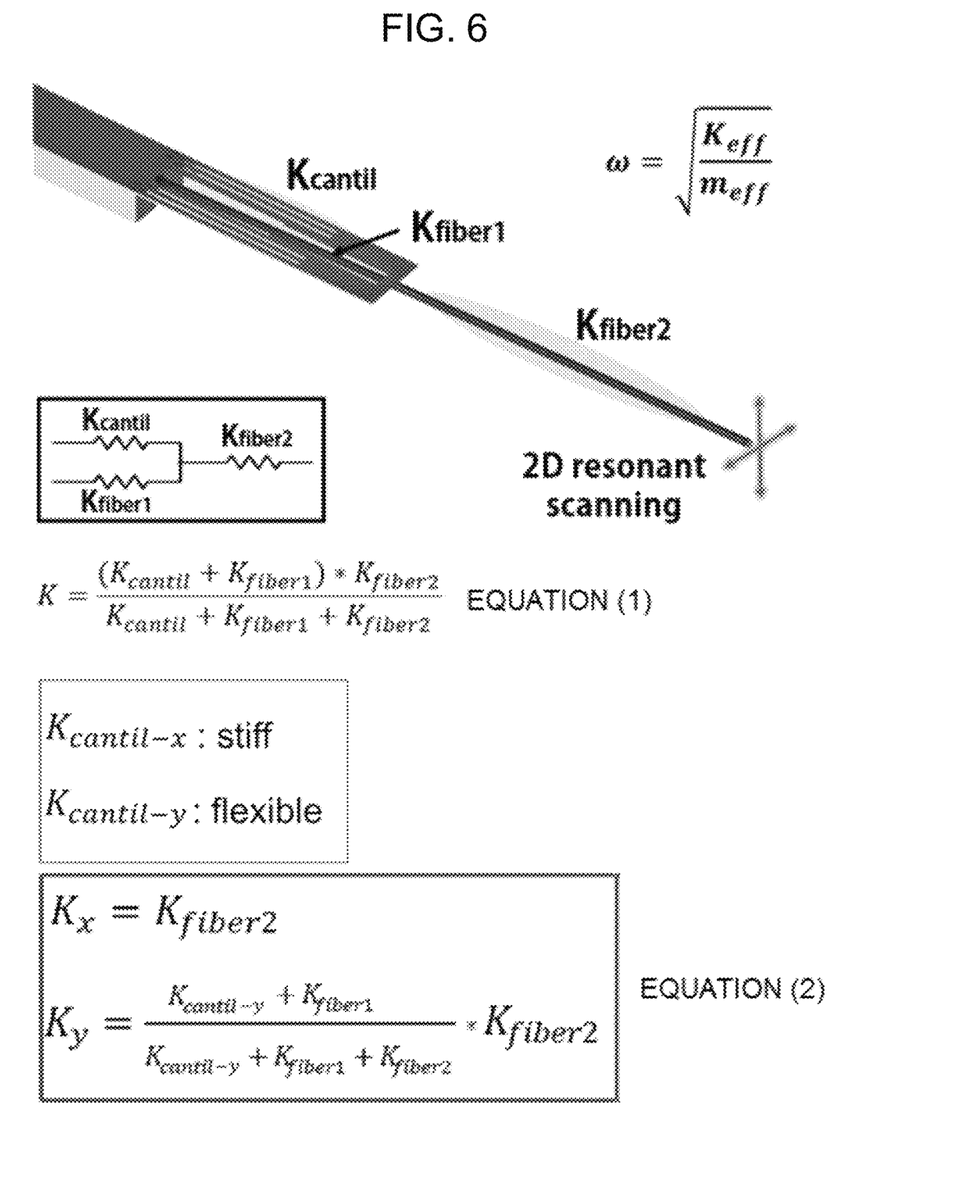
FIG. 6 is a view and equations showing rigidity in an X axis direction and rigidity in a Y axis direction according to an exemplary embodiment of the present invention.

In more detail, as shown in FIG. 6, rigidity $K_{cantil-x}$ in the X axis direction, and rigidity $K_{cantil-y}$, in the Y axis direction, of portions of the driving arms 300 and the second fixing part 200 formed in the cantilever shape are different from each other by a shape in which widths and thicknesses of the driving arms 300 are different from each other, and rigidity $K_{fiber2}$, in the X axis direction, and rigidity $K_{fiber2}$, in the Y axis direction, of a portion of the optical fiber 400 extended from the second fixing part 200 and formed in the cantilever shape are the same as each other.

Here, the entire rigidity K of portions at which portions of the driving arms 300 having the cantilever shape, including the second fixing part 200, and the optical fiber 400 are coupled to each other may be calculated by Equation (1) as shown, and it may be appreciated that the entire rigidity $K_x$ in the X axis direction and the entire rigidity $K_y$ in the Y axis direction are different from each other.

Here, as in Equation (2), rigidity $K_{cantil-x}$ of the scanner 1000 in the X axis direction is large and the scanner 1000 has a resonance frequency of about 20,000 Hz, the entire rigidity $K_x$ of the scanner 1000 in the X axis direction may be represented by $K_{fiber2}$, which is rigidity of a portion of the optical fiber 400 having a shape in which it is extended from the second fixing part 200, and the entire rigidity $K_y$ of the scanner 1000 in the Y axis direction is smaller, such that the scanner 1000 is flexible and has a resonant frequency of about 1,000 Hz. Therefore, the entire rigidity $K_y$ of the scanner 1000 in the Y axis direction may be represented by the sum of $K_{cantil-y}$ which is rigidity of the portions of the driving arms 300 having the cantilever shape, including the second fixing part 200, $K_{fiber1}$, which is rigidity of a portion of the optical fiber 400 having both ends fixed to the first and second fixing parts 100 and 200, and $K_{fiber2}$, which is the rigidity of the portion of the optical fiber 400 having the cantilever shape in which it is extended from the second fixing part 200.

In addition, a spring constant $K_x$ of an X axis direction structure and a spring constant $K_y$ of a Y axis direction structure may be different from each other. That is, spring constants of the scanner 1000 in the X and Y axis directions may be different from each other by the portions of the driving arms 300 having the cantilever shape, including the second fixing part 200.

Here, resonance frequencies of the optical fiber 400 in the X and Y axis directions may be separated from each other by a difference between the spring constants. That is, resonance frequencies of the scanner 1000 in the X and Y axis directions may be separated from each other by a shape of portions of the driving arms 300 having the different spring constants in the X and Y axis directions and having the cantilever shape. As a result, resonance frequencies, in the X and Y axis directions, of the portion of the optical fiber 400 extended from the second fixing part 200 are separated from each other, such that two-dimensional scanning may be implemented using the resonance frequencies.

In addition, two sets of driving arms 300 may be spaced apart from each other and be disposed in a pair, two end portions of the driving arms 300 fixed to the second fixing part 200 and formed as one set may be electrically connected to each other, such that the two sets of driving arms 300 are electrically connected to each other, respectively, and the optical fiber 400 may be disposed in parallel with a pair of driving arms 300 between the pair of driving arms 300 and be disposed at the height different from that of the driving arms 300 in the height direction.

That is, although the two-dimensional driving is possible even in the case in which only one set of driving arms 300 is formed, the two sets of driving arms 300 are formed in a pair as shown, such that the two-dimensional driving may be implemented using only one of the two sets of driving arms 300, if necessary, or be implemented by applying different currents to the two sets of driving arms 300. In addition, the driving arms 300 to which a current is not applied may also be formed in any shape.

Hereinafter, an operation principle of the scanner 1000 for two-dimensional optical scanning according to an exemplary embodiment of the present invention will be described.

Figure 7:
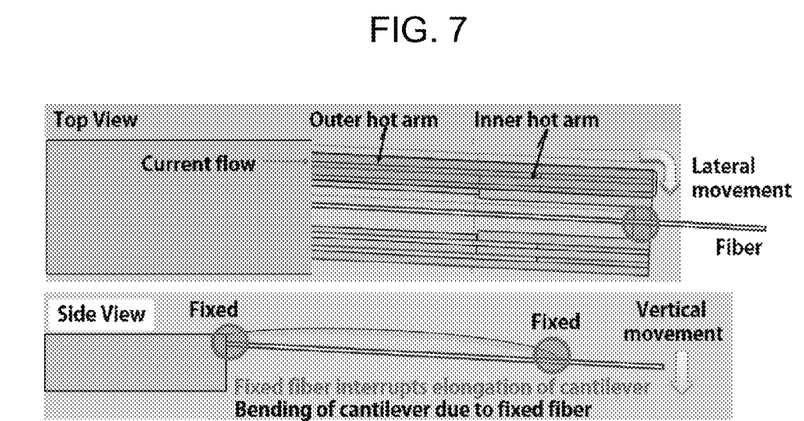
FIG. 7 is a schematic view showing an operation principle of the scanner for two-dimensional optical scanning according to an exemplary embodiment of the present invention.
Figure 8:
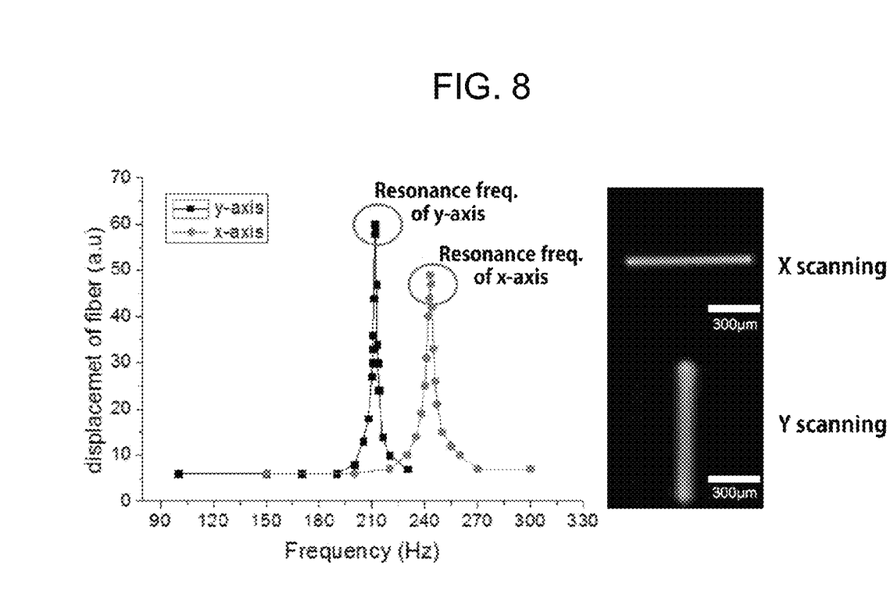
FIG. 8 is a graph and a photograph showing resonance frequencies and scanning patterns of the scanner for two-dimensional optical scanning according to an exemplary embodiment of the present invention in the X axis direction and the Y axis direction.

Here, when the current is applied to one set of driving arms 300, movement of the second fixing part 200 in the X and Y axis directions may occur by thermal expansion of the driving arms 300. That is, as shown in FIG. 7, when a current including a frequency component is applied to one of the two sets of driving arms 300 formed in a pair, force that is to bend the driving arms 300 in the X axis direction through the thermal expansion of the driving arms 300 acts on the driving arms 300. Therefore, the optical fiber 400 having both ends fixed to the first and second fixing parts 100 and 200 hinders the thermal expansion of the driving arms 300, such that force that is to bend the driving arms 300 in the Y axis direction acts on the driving arms 300 together with the force that is to bend the driving arms 300 in the X axis direction. Therefore, when a current including the resonance frequency in the X axis direction or the resonance frequency in the Y axis direction is applied to the driving arms 300, the movement of the second fixing part 200 in the X and Y axis directions occurs, such that a free end of the optical fiber 400 having the cantilever shape may perform the two-dimensional scanning while moving on an XY plane. Here, as shown in FIG. 8, the scanner 1000 for two-dimensional optical scanning according to an exemplary embodiment of the present invention may perform scanning in the X axis direction when the resonance frequency in the X axis direction is applied thereto and perform scanning in the Y axis direction when the resonance frequency in the Y axis direction is applied thereto. In addition, the driving arms 300 may also be configured to be driven by static electricity or static magnetism, in addition to a scheme in which they are thermally expanded by the current applied thereto, thereby implementing the two-dimensional scanning.

Figure 9:
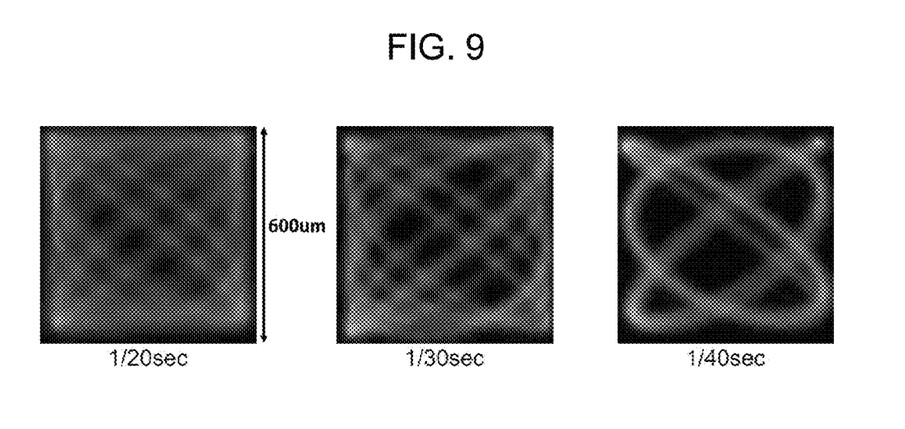
FIG. 9 is photographs showing scanning patterns of the scanner for two-dimensional optical scanning according to an exemplary embodiment of the present invention.

In addition, the current may include the resonance frequency in the X axis direction or the resonance frequency in the Y axis direction or include both of the resonance frequency in the X axis direction and the resonance frequency in the Y axis direction. That is, although the movement in the X and Y axis directions occurs (between 0 and 90 degrees at an angle of about 45 degrees in a downward direction) even in the case in which the current that does not include the frequency component is applied to the driving arms 300 as it is, larger movement occurs when the current that includes the resonance frequency component is applied to the driving arms 300. In this case, the scanning in the X axis direction is possible when the resonance frequency in the X axis direction is applied, and the scanning in the Y axis direction is possible when the resonance frequency in the Y axis direction is applied. In addition, when both of the resonance frequency in the X axis direction and the resonance frequency in the Y axis direction are included in the current applied to one set of driving arms 300, the two-dimensional driving may be implemented by one input signal without the additional structure for modulating the resonance frequency, and it may be confirmed that the optical fiber scans all of the objects within a predetermined region range, as shown in FIG. 9. In addition, Lissajous scanning may be implemented as in a shown scanning pattern, such that high resolution imaging is possible, which is advantageous at the time of endoscope imaging having much movement.

In addition, the first fixing part 100 may include the insulating layer 120 formed on the fixing block 110, wherein the insulating layer 120 may have one ends of the driving arms 300 fixed to the upper side thereof. That is, the first fixing part 100 to which one ends of the driving arms 300 are fixed may be formed in a shape in which the insulating layer 120 is formed on the fixing block 110 and one ends of the driving arms 300 are fixed to the upper side of the insulating layer 120 so that one ends of the driving arms 300 are not electrically connected to each other.

In addition, the fixing block 110 and the insulating layer 120 of the first fixing part 100, the driving arms 300, and the second fixing part 200 may be assembled to each other to form one piece. That is, a silicon-on-insulator (SOI) wafer is etched to remove unnecessary portions, such that the first fixing part 100, the driving arms 300, and the second fixing part 200 may be assembled to each other to form one piece. This will be described in detail in the following description for a manufacturing method of a scanner.

In addition, the first fixing part 100 may have the fixing groove 111 formed at a lower side thereof, and one side of the optical fiber 400 may be inserted into and fixed to the fixing groove 111 and the other side thereof may be fixed to the lower surface of the second fixing part 200. That is, one side of the optical fiber 400 may be fixed to the fixing groove 111 formed at the lower side of the first fixing part 100 and the other side thereof may be fixed to the lower surface of the second fixing part 200 in order for the optical fiber 400 to be disposed at the lower side of the driving arms 300, which is a height different from that of the driving arms 300.

In addition, the driving arms 300 may have electrodes 500 attached to one ends thereof fixed to the first fixing part 100. That is, the electrodes 500 may be attached to one ends of the driving arms 300 fixed to the first fixing part 100 so that electric wires for applying the current may be connected to the driving arms 300. Here, the electrode 500 may be made of a metal such as aluminum, or the like. However, the electrode 500 is not limited to being made of the metal, but may be variously formed.

In addition, the scanner 1000 for two-dimensional optical scanning according to an exemplary embodiment of the present invention may further include connecting parts 600 having both ends connected and fixed to the first and second fixing parts 100 and 200. That is, the driving arms 300 and the optical fiber 400 fixed to the second fixing part 200 may be stably supported by the connecting parts 600 connecting the first and second fixing parts 100 and 200 to each other, and the resonance frequency in the X axis direction and the resonance frequency in the Y axis direction may be modulated by shapes of the connecting parts 600.

In addition, although not shown, the scanner 1000 for two-dimensional optical scanning according to an exemplary embodiment of the present invention may serve as a driver moving an object such as a lens, a camera, or the like, by connecting and fixing both ends of a rod, or a wire, or the like, to the first and second fixing parts 100 and 200, fixing the object to the second fixing part 200, and then controlling the current applied to the driving arms 300. Particularly, the scanner 1000 for two-dimensional optical scanning according to an exemplary embodiment of the present invention may serve as a lens scanner when it uses the lens.

Figure 10:
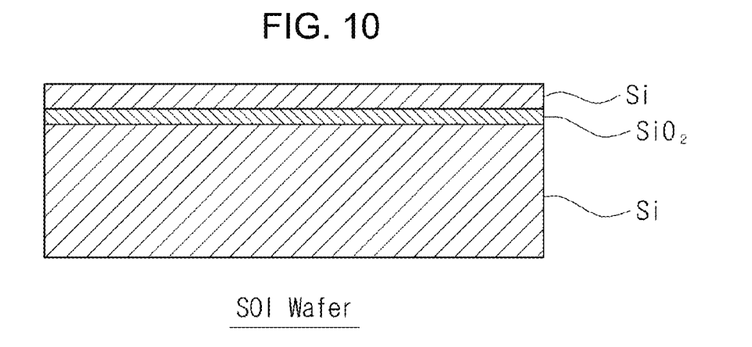
FIGS. 10 to 15 are schematic cross-sectional views showing each step of a manufacturing method of a scanner for two-dimensional optical scanning according to an exemplary embodiment of the present invention.
Figure 15:
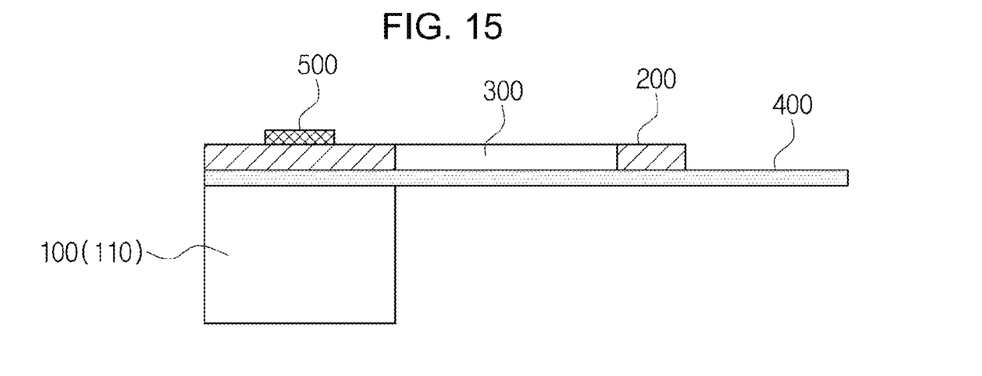

In addition, FIGS. 10 and 15 are schematic cross-sectional views showing each step of a manufacturing method of a scanner for two-dimensional optical scanning according to an exemplary embodiment of the present invention and show a cross section of the fixing groove 111 of the first fixing part 100 taken in the length direction.

As shown, the manufacturing method of a scanner for two-dimensional optical scanning according to an exemplary embodiment of the present invention may be configured to include preparing a silicon-on-insulator (SOI) wafer in which a silicon dioxide layer $SiO_2$ is formed between a lower silicon layer Si and an upper silicon layer Si (S10); etching a portion of the upper silicon layer to form shapes of the driving arms 300 and the second fixing part 200 (S20); etching a portion of the lower silicon layer to form the first fixing part 100 and forming the fixing groove 111 in the first fixing part 100 (S30); etching the silicon dioxide layer exposed by the etched portion of the lower silicon layer to form a shape in which both ends of the driving arms 300 are connected to the first and second fixing parts 100 and 200 (S40); and inserting and fixing one side of the optical fiber 400 into the fixing groove 111 of the first fixing part 100 and fixing the other side of the optical fiber 400 to the lower surface of the second fixing part 200 (S50).

That is, in the manufacturing method of a scanner for two-dimensional optical scanning according to an exemplary embodiment of the present invention, the scanner may be manufactured by etching the SOI wafer through a micro electro mechanical systems (MEMS) process (a semiconductor fine process in which processes such as a depositing process, an etching process, and the like, are repeated) and coupling the optical fiber 400 to the etched SOI wafer.

Figure 12:
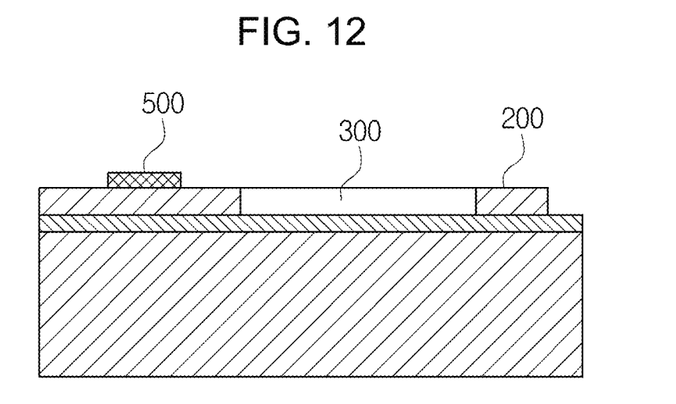

First, the silicon-on-insulator (SOI) wafer in which the silicon dioxide layer $SiO_2$ is formed between the lower silicon layer and the upper silicon layer is prepared, as shown in FIG. 10, and a portion of the upper silicon layer in the SOI wafer is etched to form the shapes of the driving arms 300 and the second fixing part 200, as shown in FIG. 12. Here, mask patterns are formed on the upper silicon layer, and exposed portions of the upper silicon layer are etched using a deep reactive ion etching (DRIE) method, thereby making it possible to form the driving arms 300 and the second fixing part 200 having a desired shape.

Figure 13:
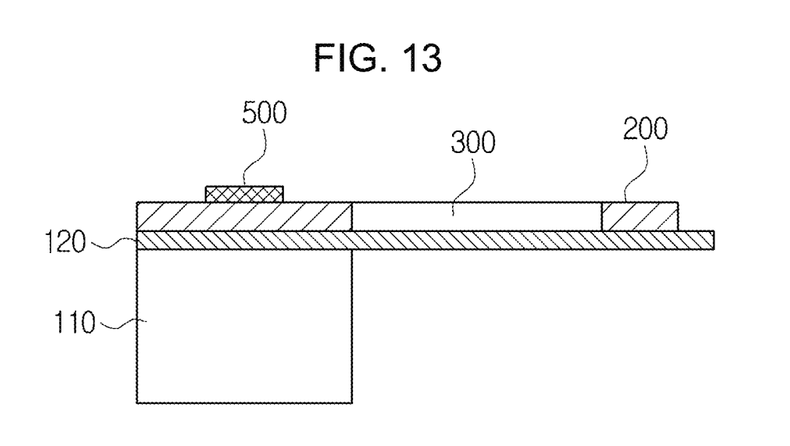

In addition, as shown in FIG. 13, a portion of the lower silicon layer may be etched to form the first fixing part 100 including the fixing groove 111. Likewise, mask patterns are formed beneath the lower silicon layer, and exposed portions of the lower silicon layer are etched using a DRIE method, thereby making it possible to form the first fixing part 100 having a desired shape.

Figure 14:
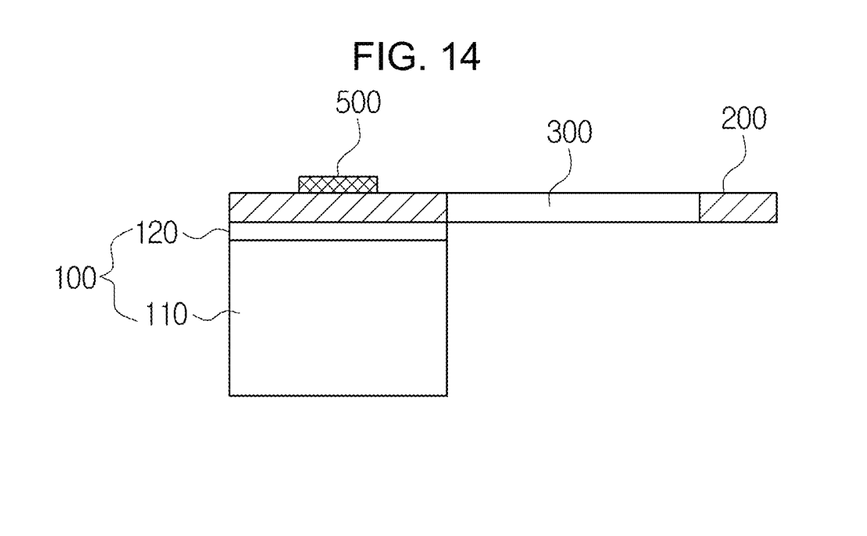

In addition, as shown in FIG. 14, the silicon dioxide layer exposed by the etched portion of the lower silicon layer may be etched to form the shape in which both ends of the driving arms 300 are connected to the first and second fixing parts 100 and 200. That is, one ends of the driving arms 300 are fixed to the first fixing part 100 and the second fixing part 200 is coupled to the other ends of the driving arms 300 in a shape in which the second fixing part 200 is formed integrally with the other ends of the driving arms 300, such that the cantilever shape may be formed. Here, at the time of etching the silicon dioxide layer, the silicon dioxide layer below the driving arms 300 and the second fixing part 200 except for a portion fixed to the first fixing part 100 may be etched and removed, and the silicon dioxide layer corresponding to the fixing groove 111 of the first fixing part 100 may also be etched and removed.

Then, as shown in FIG. 15, one side of the optical fiber 400 is inserted and fixed into the fixing groove 111 of the first fixing part 100 and the other side of the optical fiber 400 is fixed to the lower surface of the second fixing part 200, such that the scanner for two-dimensional optical scanning according to an exemplary embodiment of the present invention may be manufactured.

Therefore, the manufacturing method of a scanner for two-dimensional optical scanning according to an exemplary embodiment of the present invention may miniaturize the scanner through compact packaging, such that it may be used in a micro-miniature system such as an endoscope and may manufacture the scanner using the MEMS process, thereby making it possible to increase precision of the scanner and manufacture the scanner in various shapes and at a low cost.

Here, the first and second fixing parts 100 and 200 may be formed so as to be spaced apart from each other, the two or more driving arms 300 may be formed as a set, be formed so that the end portions thereof fixed to the second fixing part 200 are electrically connected to each other, and be formed so that the resonance frequency in the X axis direction and the resonance frequency in the Y axis direction are different from each other, and the optical fiber 400 may be disposed so as to be spaced apart from one side of the driving arms 300 in the width direction and be disposed at the height different from that of the driving arms 300 in the height direction.

In addition, the two sets of driving arms 300 may be spaced apart from each other and be disposed in a pair, two end portions of the driving arms 300 fixed to the second fixing part 200 and formed as one set may be electrically connected to each other, such that the two sets of driving arms 300 are electrically connected to each other, respectively, and the optical fiber 400 may be disposed between the pair of driving arms 300 and be disposed at the height different from that of the driving arms 300 in the height direction.

That is, as described above, the upper silicon layer is etched after the mask patterns are formed so that the driving arms 300 and the second fixing part 200 are formed in a shape in which they are connected to each other at the time of etching the upper silicon layer, such that the end portions of the two driving arms 300 formed as one set may be electrically connected to each other by the second fixing part 200. Here, the two or more driving arms 300 may be formed as one set, and only one set of driving arms 300 may be formed or two sets of driving arms 300 may be formed in a shape in which they are spaced apart from each other and are disposed in a pair.

Figure 11:
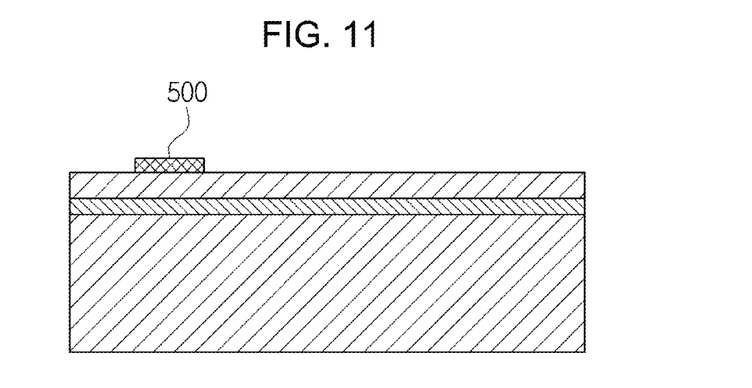

In addition, the manufacturing method of a scanner for two-dimensional optical scanning according to an exemplary embodiment of the present invention may further include attaching the electrodes 500 to one ends of the driving arms 300 fixed to the first fixing part 100 (S15). That is, the electrodes 500 are made of a metal such as aluminum, or the like, are and attached to one ends of the driving arms 300 fixed to the first fixing part 100, thereby making it possible to facilitate connection of electric wires for supplying power. Here, the electrodes 500 may be attached before etching the upper silicon layer, as shown in FIG. 11, or may be formed at the end portions of the driving arms 300, respectively, after etching the upper silicon layer.

Figure 16:
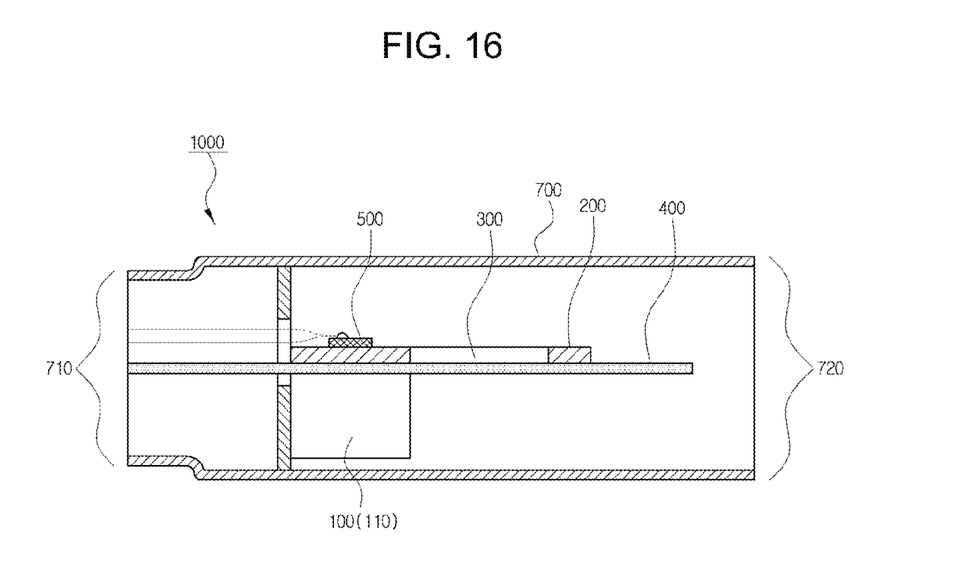
FIGS. 16 to 19 are schematic cross-sectional views showing examples of scanners for two-dimensional optical scanning including a probe body according to an exemplary embodiment of the present invention.

In addition, the scanner 1000 for two-dimensional optical scanning according to an exemplary embodiment of the present invention may further include a probe body 700 having an internal space formed therein so as to accommodate the first fixing part 100, the second fixing part 200, the driving arms 300, and the optical fiber 400 therein and including a light input part 710 and a light output part 720.

That is, as shown in FIG. 16, the first fixing part 100, the second fixing part 200, the driving arms 300, and the optical fiber 400 may be accommodated in the probe body 700 having the light input part 710 formed at one side thereof and the light output part 720 formed at the other side thereof. Here, the probe body 700 may have a support 701 formed therein and have the optical fiber 400 positioned at the center of an inner portion thereof, and the first fixing part 100 may be coupled and fixed to the support 701.

Figure 17:
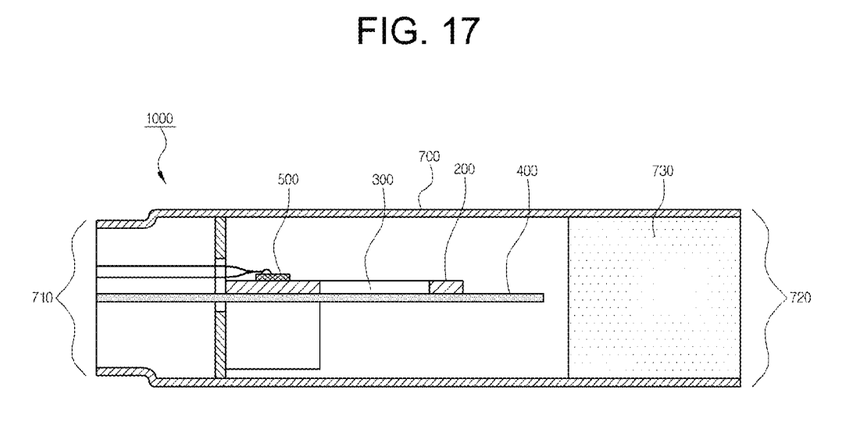

In addition, a lens unit 730 including one or more lens may be further disposed in a light path between the optical fiber 400 and the light output part 720 within the probe body 700.

That is, as shown in FIG. 17, the lens unit 730 for focusing light transmitted through the optical fiber 400 on a test target may be disposed in the light path between the optical fiber 400 and the light output part 720. Here, the lens unit 730 may be coupled and fixed to an inner peripheral surface of the probe body 700.

In addition, the lens unit 730 may include an optical lens made of a polymer material or a glass material or a graded index (GRIN) lens having refractive index distribution having a form in which light may be focused.

Figure 18:
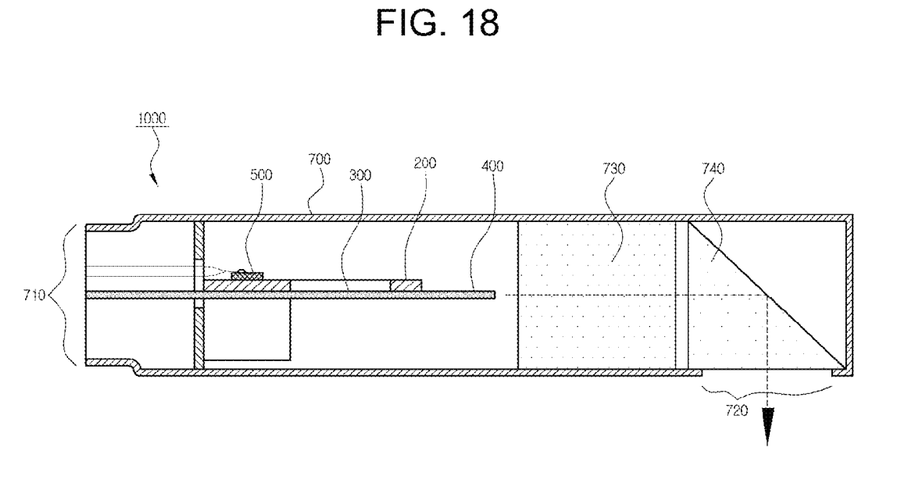
Figure 19:
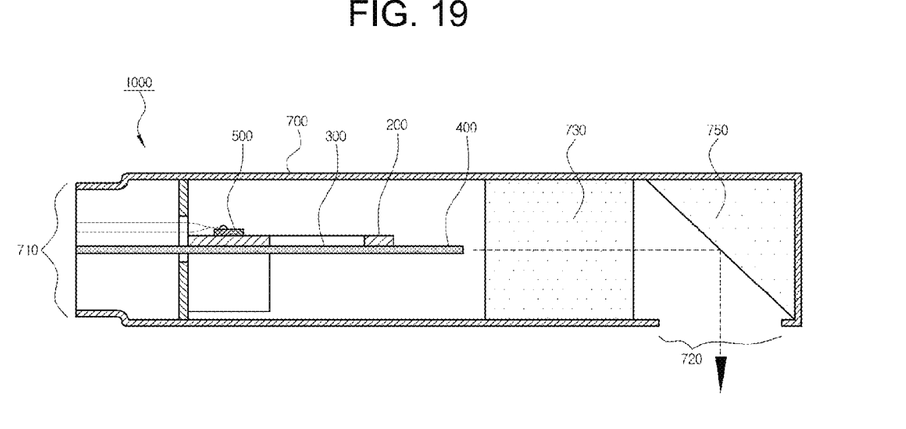

In addition, a light path changing component 740 or 750 may be further disposed between the lens unit 730 and the light output part 720 within the probe body 700. As shown in FIGS. 18 and 19, the light path changing component may be formed of a prism 740 or a reflection mirror 750. That is, the prism 740 or the reflection mirror 750 may be used in order to change a path of light output through the light output part 720, and the light may be reflected through total reflection on a surface of the prism 740 or a reflection surface of the reflection mirror 750 to change the path of the light.

Figure 20:
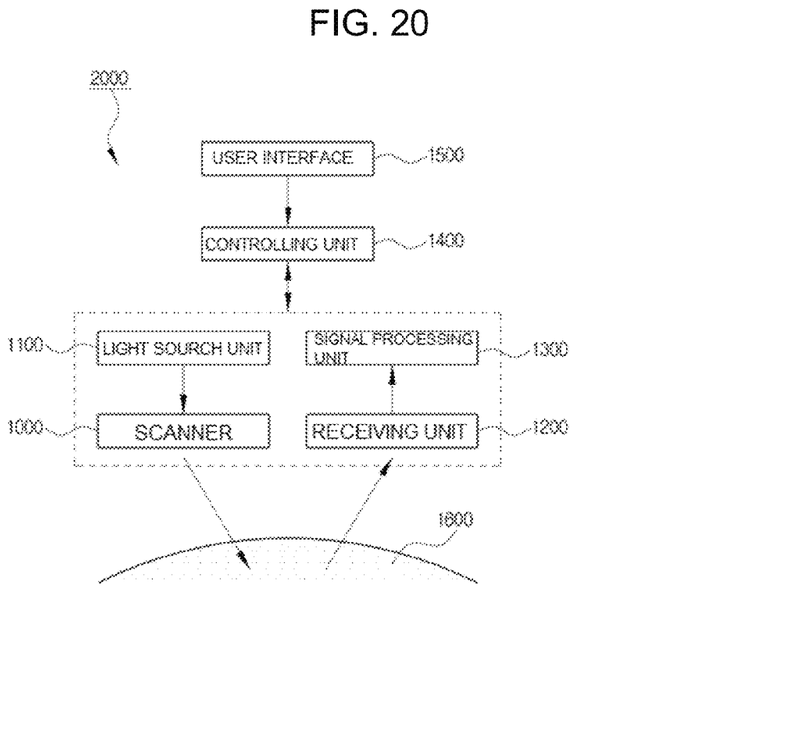
FIG. 20 is a block diagram showing a medical imaging apparatus including a scanner for two-dimensional optical scanning according to an exemplary embodiment of the present invention.

FIG. 20 is a block diagram showing a medical imaging apparatus including a scanner for two-dimensional optical scanning according to an exemplary embodiment of the present invention.

As shown in FIG. 20, the medical imaging apparatus 2000 according to an exemplary embodiment of the present invention may be configured to include a light source unit 1100; the scanner 1000 for two-dimensional optical scanning scanning-irradiating light from the light source unit 1100 to a test target 1600; a receiving unit 1200 receiving a signal generated from the test target 1600; and a signal processing unit 1300 processing the signal received by the receiving unit 1200 to generate an image signal.

Here, the scanner 1000 for two-dimensional optical scanning may have a configuration that may irradiate the light to a test target 1600 while scanning the predetermined region of the test target 1600, and various types of scanners as described above or a combination thereof may be used as the scanner 1000.

Here, when the light is irradiated to the test target 1600 through the scanner 1000 for two-dimensional optical scanning, a new signal including property information on the test target 1600 is generated and is received by the receiving unit 1200. Here, the receiving unit 1200 may also be included in the scanner 1000 for two-dimensional optical scanning. In addition, the signal processing unit 1300 serves to process the signal received by the receiving unit 1200 to generate the image signal.

In addition, the medical imaging apparatus 2000 according to an exemplary embodiment of the present invention may further include a user interface 1500 and a controlling unit 1400. The user interface 1500 may include an input unit and a display unit and transmit an input required for the controlling unit 1400 using the input unit and the display unit. In addition, the controlling unit 1400 may control the respective components configuring the medical imaging apparatus 2000 depending on a command input through the user interface 1500. For example, the controlling unit 1400 may control scanning driving of the scanner 1000 for two-dimensional optical scanning. In addition, the controlling unit 1400 may be implemented by a microprocessor, or the like.

Further, the signal processing unit 1300 may process the received signal by any one of the laser based imaging methods. Here, as the laser based imaging methods, an optical coherence tomography (OCT) method, an optical coherence microscopy (OCM) method, a confocal method, a multi-photon method, a photoacoustic tomography (PAT) method, and the like, may be used. In addition to the above-mentioned methods, various laser based imaging methods may be used.

Here, the OCT method is a coherence tomography method that may image a fine structure of a biological tissue using an interference phenomenon of light. The OCM method, which is one field of OCT, is a technology that may image information, in a depth direction, of a material having high scattering at a high resolution. The confocal method is a technology that may recognize a three-dimensional structure of a material at a high resolution using a principle of receiving only light of which a focus coincides with that of a sample from a laser, which becomes a light source. The multi-photon method, which is one of the non-linear imaging methods, is a technology that may view a material positioned at a deep place without large damage using a long wavelength having high strength. The photoacoustic tomography (PAT) method, which is a non-invasive imaging method using a photoacoustic effect, is a method that may implement a function image, a metabolism image, and a gene or biomolecule image as well as a structural image of an in vivo tissue (a tissue in a human body) using optical characteristics and ultrasonic characteristics.

Here, details of the respective components of the medical imaging apparatus 2000 according to an exemplary embodiment of the present invention may be determined so as to use the OCT method, the OCM method, the confocal method, the multi-photon method, the PAT method, and the like. That is, a detecting sensor included in the receiving unit 1200 may be changed depending on a kind of signal generated from the test target, and the signal processing unit 1300 may process the received signal depending on each method. As an example, in the case of using the PAT method, the light source unit 1100 may be a pulse laser inducing an ultrasonic wave from the test target, and the receiving unit 1200 may be an ultrasonic wave receiving unit including a transducer transducing an ultrasonic wave generated from the test target into an electrical signal.

The scanner for two-dimensional optical scanning according to an exemplary embodiment of the present invention may implement the two-dimensional driving by one input signal without an additional structure for modulating the resonance frequency.

In addition, the manufacturing method of a scanner for two-dimensional optical scanning according to an exemplary embodiment of the present invention may miniaturize the scanner through the compact packaging, such that it may be used in the micro-miniature system such as the endoscope and may manufacture the scanner using the MEMS process, thereby making it possible to increase precision of the scanner and manufacture the scanner in various shapes and at a low cost.

Further, the scanner for two-dimensional optical scanning according to an exemplary embodiment of the present invention is used in the medical imaging apparatus, thereby making it possible to provide a medical image having improved quality without crosstalk between axes (interference between movement in the X axis direction and movement in the Y axis direction) through separation of the resonance frequencies.

The present invention is not limited to the above-mentioned exemplary embodiments, and may be variously applied, and may be variously modified without departing from the gist of the present invention claimed in the claims.

What is claimed is:

1. A scanner for two-dimensional optical scanning, comprising:
   a first fixing part;
   a second fixing part disposed so as to be spaced apart from the first fixing part;
   two or more driving arms having both ends connected and fixed to the first and second fixing parts, formed as one set and formed so that end portions thereof fixed to the second fixing part are electrically connected to each other, and formed so that a resonance frequency in an X axis direction and a resonance frequency in a Y axis direction are different from each other; and
   an optical fiber having one side fixed to the first fixing part and the other side fixed to the second fixing part, disposed so as to be spaced apart from one side of the driving arms in a width direction, and disposed at a height different from that of the driving arms in a height direction,
   wherein a spring constant of an X axis direction structure and a spring constant of a Y axis direction structure are different from each other, and
   wherein resonance frequencies of the optical fiber in the X and Y axis directions are separated from each other by a difference between the spring constants.

2. The scanner for two-dimensional optical scanning of claim 1, wherein when a current is applied to one set of driving arms, movement of the second fixing part in the X and Y axis directions occurs by thermal expansion of the driving arms.

3. The scanner for two-dimensional optical scanning of claim 1, wherein the first fixing part includes an insulating layer formed on a fixing block, the insulating layer having one ends of the driving arms fixed to an upper side thereof.

4. The scanner for two-dimensional optical scanning of claim 1, wherein the first fixing part has a fixing groove formed at a lower side thereof, and one side of the optical fiber is inserted into and fixed to the fixing groove and the other side thereof is fixed to a lower surface of the second fixing part.

5. The scanner for two-dimensional optical scanning of claim 1, wherein the driving arms have electrodes attached to one ends thereof fixed to the first fixing part.

6. The scanner for two-dimensional optical scanning of claim 1, further comprising connecting parts having both ends connected and fixed to the first and second fixing parts.

7. The scanner for two-dimensional optical scanning of claim 1, further comprising a probe body having an internal space formed therein so as to accommodate the first fixing part, the second fixing part, the driving arms, and the optical fiber therein and including a light input part and a light output part.

8. A scanner for two-dimensional optical scanning, comprising:
   a first fixing part;
   a second fixing part disposed so as to be spaced apart from the first fixing part;
   two or more driving arms having both ends connected and fixed to the first and second fixing parts, formed as one set and formed so that end portions thereof fixed to the second fixing part are electrically connected to each other, and formed so that a resonance frequency in an X axis direction and a resonance frequency in a Y axis direction are different from each other; and
   an optical fiber having one side fixed to the first fixing part and the other side fixed to the second fixing part, disposed so as to be spaced apart from one side of the driving arms in a width direction, and disposed at a height different from that of the driving arms in a height direction,
   wherein two sets of driving arms are spaced apart from each other and are disposed in a pair, two end portions of the driving arms fixed to the second fixing part and formed as one set are electrically connected to each other, such that the two sets of driving arms are electrically connected to each other, respectively, and the optical fiber is disposed between a pair of driving arms and is disposed at the height different from that of the driving arms in the height direction.

9. A scanner for two-dimensional optical scanning, comprising:
a first fixing part;
a second fixing part disposed so as to be spaced apart from the first fixing part;
two or more driving arms having both ends connected and fixed to the first and second fixing parts, formed as one set and formed so that end portions thereof fixed to the second fixing part are electrically connected to each other, and formed so that a resonance frequency in an X axis direction and a resonance frequency in a Y axis direction are different from each other; and
an optical fiber having one side fixed to the first fixing part and the other side fixed to the second fixing part, disposed so as to be spaced apart from one side of the driving arms in a width direction, and disposed at a height different from that of the driving arms in a height direction,
wherein when a current is applied to one set of driving arms, movement of the second fixing part in the X and Y axis directions occurs by thermal expansion of the driving arms; and
wherein the current includes the resonance frequency in the X axis direction or the resonance frequency in the Y axis direction or includes both of the resonance frequency in the X axis direction and the resonance frequency in the Y axis direction.

10. A scanner for two-dimensional optical scanning, comprising:
a first fixing part;
a second fixing part disposed so as to be spaced apart from the first fixing part;
two or more driving arms having both ends connected and fixed to the first and second fixing parts, formed as one set and formed so that end portions thereof fixed to the second fixing part are electrically connected to each other, and formed so that a resonance frequency in an X axis direction and a resonance frequency in a Y axis direction are different from each other; and
an optical fiber having one side fixed to the first fixing part and the other side fixed to the second fixing part, disposed so as to be spaced apart from one side of the driving arms in a width direction, and disposed at a height different from that of the driving arms in a height direction,
wherein the first fixing part includes an insulating layer formed on a fixing block, the insulating layer having one ends of the driving arms fixed to an upper side thereof and wherein the fixing block and the insulating layer of the first fixing part, the driving arms, and the second fixing part are assembled to each other to form one piece.

11. A scanner for two-dimensional optical scanning, comprising:
a first fixing part;
a second fixing part disposed so as to be spaced apart from the first fixing part;
two or more driving arms having both ends connected and fixed to the first and second fixing parts, formed as one set and formed so that end portions thereof fixed to the second fixing part are electrically connected to each other, and formed so that a resonance frequency in an X axis direction and a resonance frequency in a Y axis direction are different from each other;
an optical fiber having one side fixed to the first fixing part and the other side fixed to the second fixing part, disposed so as to be spaced apart from one side of the driving arms in a width direction, and disposed at a height different from that of the driving arms in a height direction; and
a probe body having an internal space formed therein so as to accommodate the first fixing part, the second fixing part, the driving arms, and the optical fiber therein and including a light input part and a light output part,
wherein a lens unit including one or more lens is further disposed in a light path between the optical fiber and the light output part within the probe body.

12. The scanner for two-dimensional optical scanning of claim 11, wherein the lens unit includes a graded index (GRIN) lens.

13. The scanner for two-dimensional optical scanning of claim 11, wherein a light path changing component is further disposed between the lens unit and the light output part within the probe body.

14. The scanner for two-dimensional optical scanning of claim 13, wherein the light path changing component is formed of a reflection mirror.

15. The scanner for two-dimensional optical scanning of claim 13, wherein the light path changing component is formed of a prism.

16. A medical apparatus comprising:
a light source unit;
the scanner for two-dimensional optical scanning of claim 1 scanning-irradiating light from the light source unit to a test target;
a receiving unit receiving a signal generated from the test target; and
a signal processing unit processing the signal received by the receiving unit to generate an image signal.

* * * * *